(12) United States Patent
Pedrazzini (10) Patent No.: US 8,463,427 B2
(45) Date of Patent: Jun. 11, 2013

(54) AUTOMATIC APPARATUS FOR LOADING AND UNLOADING BIOLOGICAL MATERIAL TEST TUBES IN A PNEUMATIC MAIL SYSTEM

(75) Inventor: Gianandrea Pedrazzini, Paradiso (CH)

(73) Assignee: Inpeco Holding Ltd., Valletta (MT)

( * ) Notice: Subject to any disclaimer, the term of this patent is extended or adjusted under 35 U.S.C. 154(b) by 448 days.

(21) Appl. No.: 12/745,482

(22) PCT Filed: Nov. 26, 2008

(86) PCT No.: PCT/EP2008/066262
§ 371 (c)(1),
(2), (4) Date: May 28, 2010

(87) PCT Pub. No.: WO2009/068574
PCT Pub. Date: Jun. 4, 2009

(65) Prior Publication Data
US 2010/0312379 A1 Dec. 9, 2010

(30) Foreign Application Priority Data

Nov. 30, 2007 (IT) .............................. MI2007A2255

(51) Int. Cl.
*G06F 7/00* (2006.01)
*B66C 1/00* (2006.01)
(52) U.S. Cl.
USPC ........... 700/230; 700/213; 700/216; 700/218; 700/219; 700/223; 700/228; 700/227; 414/730
(58) Field of Classification Search
None
See application file for complete search history.

(56) References Cited

U.S. PATENT DOCUMENTS

| 4,160,382 | A | 7/1979 | Finsterwalder et al. |
| 4,526,045 | A | 7/1985 | Reekie |
| 6,060,022 | A | 5/2000 | Pang et al. |
| 6,062,398 | A | 5/2000 | Thalmayr |
| 7,141,213 | B1 * | 11/2006 | Pang et al. ...................... 422/65 |
| 2007/0196236 | A1 | 8/2007 | Richter |

FOREIGN PATENT DOCUMENTS

| EP | 0 650 056 A1 | 4/1995 |
| FR | 2 888 328 A1 | 1/2007 |
| GB | 1 323 530 A | 7/1973 |
| WO | WO 02/41823 A2 | 5/2002 |

* cited by examiner

*Primary Examiner* — Gene Crawford
*Assistant Examiner* — Yolanda Jones
(74) *Attorney, Agent, or Firm* — Birch, Stewart, Kolasch & Birch, LLP (57) ABSTRACT

An apparatus and method adapted to automatically load and unload biological material test tubes into and from a capsule suitable for handling in a pneumatic mail system, the test tubes being supported by a test tube container which may be removably accommodated in the capsule, wherein the apparatus includes a loading and unloading interface, a receiving/dispatching station for conveying capsules to/from various biological material collection departments and a receiving/dispatching station for conveying capsules to/from biological material testing departments, and devices adapted to handle arriving test tube containers and test tubes to be dispatched to a bench, including a loading area and an unloading area for test tubes and test tube containers, arriving material identifying and checking devices and orienting devices for test tube containers, including a control unit adapted to coordinate the devices during the loading and unloading operations.

6 Claims, 7 Drawing Sheets

AUTOMATIC APPARATUS FOR LOADING AND UNLOADING BIOLOGICAL MATERIAL TEST TUBES IN A PNEUMATIC MAIL SYSTEM

The present invention relates to an automatic apparatus for loading and unloading test tubes containing biological material and transported by means of a pneumatic mail system.

In facilities such as factories, banks, supermarkets and hospitals, there is a great need for transporting materials, such as for example production samples, money, documents, medicaments and laboratory specimens.

A pneumatic mail system is a concrete solution to the several problems related to the transportation of materials in a facility.

A pneumatic mail system is a light, internal transportation system, capable of ensuring the automated handling of small-sized commodities, in a rapid and safe manner. Such a system consists of intercommunicating dispatching and receiving stations, connected by a network of pipes. The commodities are inserted in specific containers, which are transported inside the line by a suitably created air flow, generated by a turbine.

The receiving/dispatching stations are generally provided with automatic starting device and pneumatic brake for the arriving containers. There is no emission of air, neither at the arrival nor at the departure, thus complying with the strictest hygienic requirements. The pipes allow to connect several points in a building, and even between different buildings, by using overhead and underground paths.

The turbines may work either by pressure or by suction, thus allowing even high transportation speeds suited to the type of transported material.

Diverters between pipes serve a function similar to the switches of a train track and allow to create even highly complex systems. Being electronically controlled and automatically positioned, the diverters allow the containers to reach the chosen destinations.

A modern pneumatic mail system may be used in various fields, such as, for example, in the industrial field for the transportation of production materials, in the banking field for the transportation of money, and in the hospital field for the transportation of medicaments or biological materials.

In the hospital field, which is the scope of the present invention, the adoption of the system ensures the constant connection between departments which are even several hundreds of meters apart, thus respecting the required handling times, increasing the facility automation, and ensuring the maximum safety even in transporting delicate materials.

Specifically, in the hospital field, a pneumatic mail system may be used for automatically transporting test tubes containing blood from the collecting points to the test laboratories, thus ensuring:

safety: a reserved, inaccessible path is offered to the handled material, ensuring a slow speed transportation when handling blood specimens to prevent hemolytic effects from generating;

transportation rapidity: a fast, direct handling is carried out between the various connected departments, offering the possibility of priority dispatching of the capsules in case of urgencies;

easy use: simple operations are carried out by the operators;

cost reduction: manpower costs are decreased because personnel is relieved from handling operations, with a great benefit for all medical and paramedical personnel, who can thus devote all their time to patient care;

quietness: there is no noise in the departments.

In such a pneumatic transportation process, the preparation of the container to be handled has not yet been automated.

Such an operation requires the assigned personnel to empty the received containers and fill the containers to be dispatched. Such a task, if performed manually, strongly limits the great advantages which are obtained from the use of a pneumatic mail system, both in terms of times and operator safety, if the handled material consists of test tubes containing biological material specimens.

Therefore, in order to limit manual intervention by operators involved in the handling of materials transported in the pneumatic mail systems, an apparatus aimed at automating the entire process is required, comprising filling the containers, transporting by means of pneumatic system, and subsequently emptying the same.

It is the object of the present invention to make an apparatus for loading and unloading biological material specimens transported between the various departments of a hospital facility by means of a pneumatic mail system capable of overcoming the aforesaid problems.

U.S. Pat. No. 6,606,622 discloses a work station for handling test tubes and test tube containers.

In accordance with the invention, the object is reached by an apparatus as disclosed in claim 1

It is a further object of the present invention to make an automatic method of loading and unloading biological material specimens transported between the various departments of a hospital facility by means of a pneumatic mail system capable of overcoming the aforesaid problems.

In accordance with the invention, such a further object is reached by an automatic method as disclosed in claim 5. The control unit may be an application software installed on a computer adapted to receive information and send commands to the devices operating inside the described apparatus.

The test tubes are transported inside the pneumatic mail line by means of an appropriate container, named capsule, having a shape adapted to slide in the pipes under the bias of the air flow. The capsule, after reaching a station, automatically opens allowing the handling device for test tube containers and test tubes to access it.

The described device provides for the biological material test tubes being contained, inside the capsules, in specific containers provided with twenty locations adapted to accommodate an equal number of test tubes.

The bench comprising the unloading area and the loading area is a surface interfacing with an interface area serving the function of receiving the received biological material test tubes and presenting the biological material test tubes to be dispatched by means of the pneumatic mail system. Said interface area is included in a further automation apparatus suitable for the automatic transportation to devices used for preparing and testing the biological specimens contained in the test tubes.

The unloading area comprises a test tube receiving station and a specific space in which the received test tube container is placed to be unloaded.

The receiving station present on the bench consists of an opening connected to a pipe end.

Upon the arrival of a capsule at the receiving station, an arriving material identifying and checking device verifies the actual presence of test tubes inside the container. Such a piece of information, sent to the control unit, is used by the handling device, comprising a mechanical arm, during the subsequent step of unloading the test tubes (from the containers to the interface area).

The arriving material identifying and checking device may be, for example, a camera serving the function of "photographing" the open capsule containing the test tube container.

The unloading device consists of a gripper connected to a support having the possibility of moving over the test tube unloading area and reaching all the working points needed for performing the operations.

The unloading device, if a loaded capsule arrives, picks the test tube container from the capsule and places it in the specific unloading space.

Once the test tube container has been correctly positioned, said device picks the test tubes from said container one by one, thus positioning them at the interface area.

The loading area comprises a test tube dispatching station and a specific space in which the received test tube container is placed to be loaded.

The dispatching station on the bench, equivalent to the receiving station, consists in an opening connected to a pipe end.

The capsules containing the test tube containers which reach the dispatching station are generally empty, ready to the loaded with test tubes.

Upon the arrival of a capsule at the dispatching station, the identifying and checking device verifies the actual absence of test tubes inside the container.

The loading device, functionally equivalent to the unloading device, consists of a gripper connected to a support having the possibility of moving over the test tube loading area and reaching all the working points needed for completing the operations.

The loading device, if a capsule arrives, picks the test tube container from the capsule and places it in the specific loading space.

The test tubes which need to be transported by pneumatic mail are presented at the interface area.

The same loading device, once the empty test tube container has been arranged in the correct position in the loading area, moves the arriving test tubes from the interface area to the container.

After filling the container with test tubes, it is inserted into the dispatching station by means of the loading device.

These and other features of the present invention will be further explained in the following detailed description of a practical embodiment thereof shown by way of non-limitative example in the accompanying drawings, in which.

Figure 1:
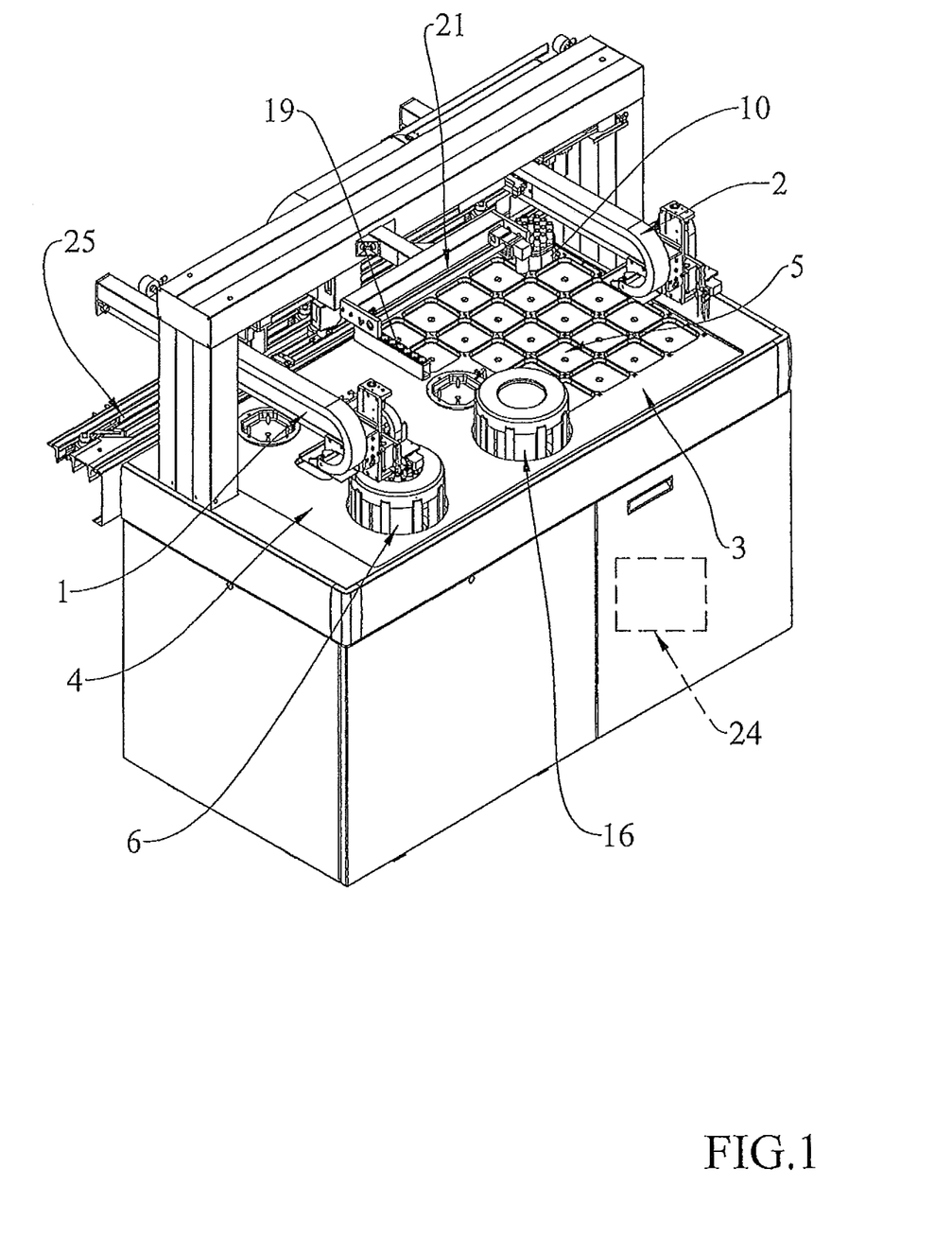
FIG. 1 shows a perspective view of the automatic apparatus adapted to load and unload the test tube.

FIG. 1 shows an apparatus adapted to load and unload biological material test tubes according to the present invention comprising a handling device 1 for test tubes and test tube containers adapted to load/unload capsules arriving at/departing from biological material collecting departments, e.g. hospital departments, and a handling device 2 for test tubes and test tube containers adapted to load/unload capsules arriving at/departing from biological material testing departments, e.g. specialized laboratory departments. Both handling devices 1 and 2 for test tubes and test tube containers comprise mechanical arms and operate on a working area consisting of a bench 3 comprising a test tube unloading area 4 and a test tube loading area 5. The devices forming the system herein described are coordinated and controlled by a control unit 24 consisting of an application software residing in a computer connected to the system located, for example, in a position underneath the bench and shielded by protective panels (FIG. 1).

Figure 8:
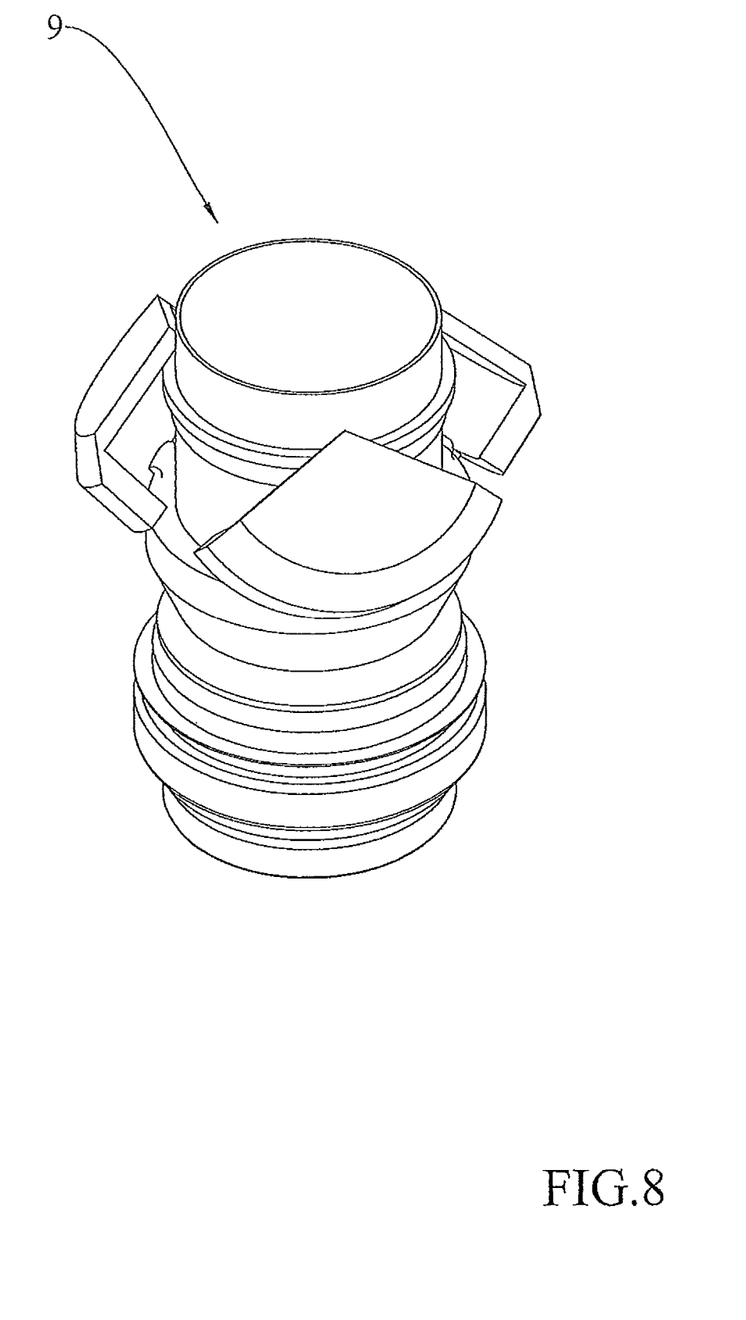
FIG. 8 shows the capsule adapted to transport the test tube containers in the pneumatic mail system.

A capsule 9 (FIG. 8) is a suitable container used in a pneumatic mail system adapted to move in the pipe network which forms such a system, under the bias of an air flow. In FIG. 8, the capsule 9 is shown in an open configuration, i.e. so as to allow to access and possibly pick the material transported therein.

Figure 6:
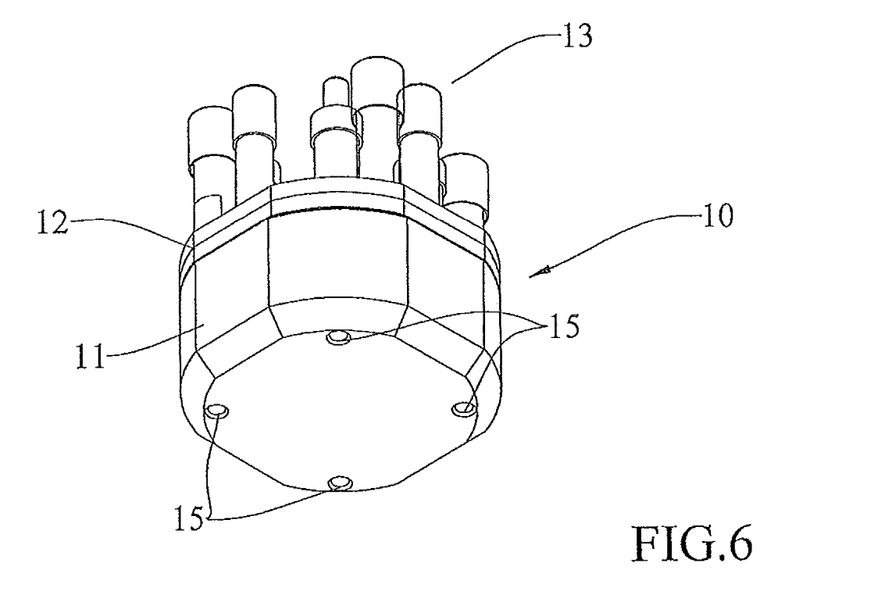
FIG. 6 shows a perspective view of the test tube container.
Figure 7:
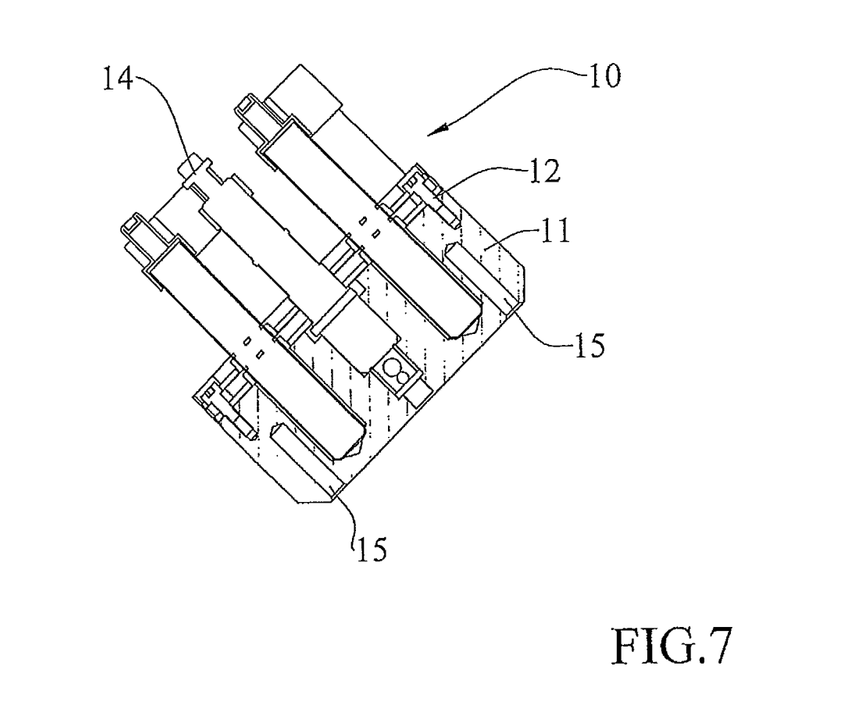
FIG. 7 shows a vertical section view of the configuration in FIG. 6.

In the suggested embodiment, the capsule 9 is adapted to transport a test tube container 10 (FIGS. 1, 6 and 7). Said container 10 consists of a main body 11 having an octagonal base on which a layer of silicone 12 is accommodated and adapted to support the test tubes 13 contained therein in a stable, vertical manner, and to dampen possible shaking during the transportation. The container 10 comprises twenty positions adapted to house an equal number of test tubes 13. In the central position with respect to the octagonal base of the container 10 there is a support 14 (FIG. 7) serving the function of allowing the handling devices 1 and 2 for test tubes and containers to pick the container during the loading and unloading processes.

Four holes 15 (FIG. 6) are present on the resting surface of the container 10, serving the function of allowing the container to be oriented by the container orienting devices 7 and 17, as will be explained below.

Figure 4:
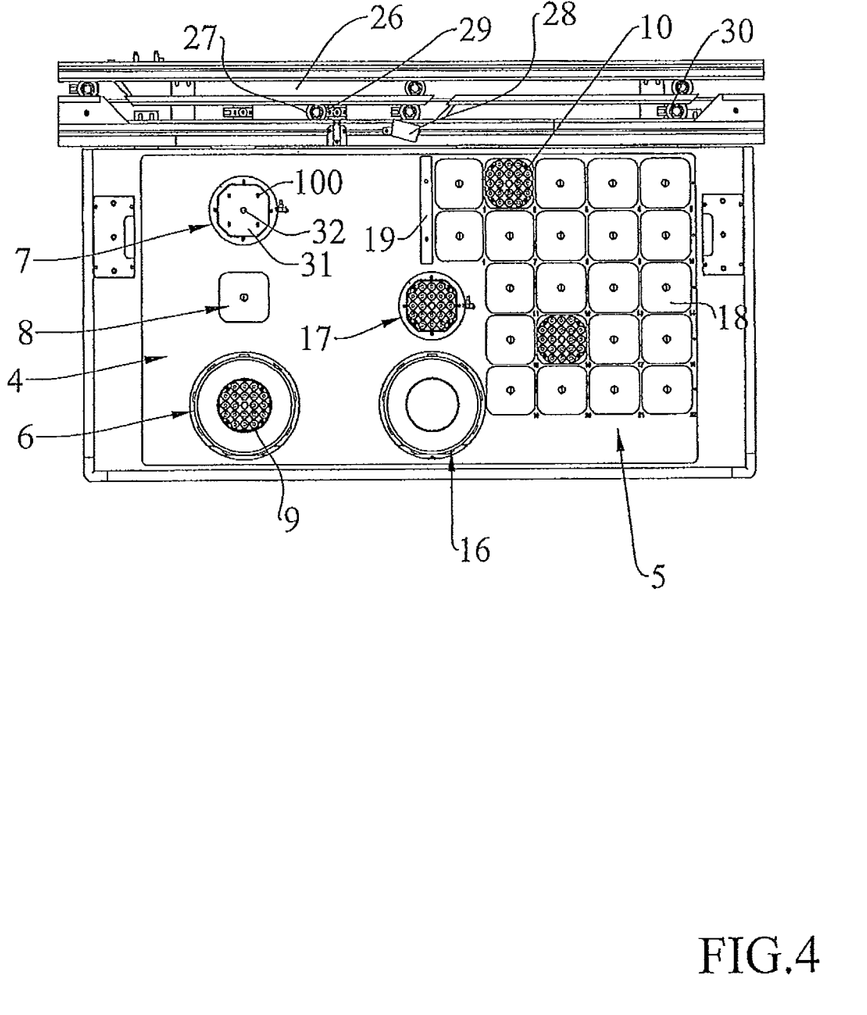
FIG. 4 shows a top plan view of the surface.

The test tube unloading area 4 consists of a capsule receiving/dispatching station 6, a container orienting device 7 and a container transit position 8 (FIG. 4). In a hospital, the capsule dispatching/receiving station 6 could be connected to the various hospital departments in which collections are made and from which the biological material test tubes are sent to be prepared and tested by the interfacing modules on the conveyor belt and possibly by other specialised test laboratories for biological material.

The test tube loading area 5 consists of a capsule receiving/dispatching station 16, a container orienting device 17, twenty-two loading positions 18 and a possible position adapted to house a linear waiting test tube container 19, as will be described below (FIG. 4). In a hospital, the capsule receiving/dispatching station 16 could be connected to the different specialized test laboratories, to which the test tubes are dispatched in the case specialized tests which are not provided by the interfacing test modules on the conveyor belt need to be performed.

When the container 10, transported by the capsule 9, arrives at the one of the two capsule receiving/dispatching stations 6 and 16, the octagonal base of the container is oriented in a random manner. The handling devices 1 and 2 for test tubes and containers correctly reach the twenty positions of the containers only if the container, horizontally arranged on bench 3, is positioned according to a certain orientation, which corresponds to two sides of the octagonal base being parallel to the side profiles of the bench (as the container shown in FIG. 4 placed in the container orienting device 17).

Figure 5:
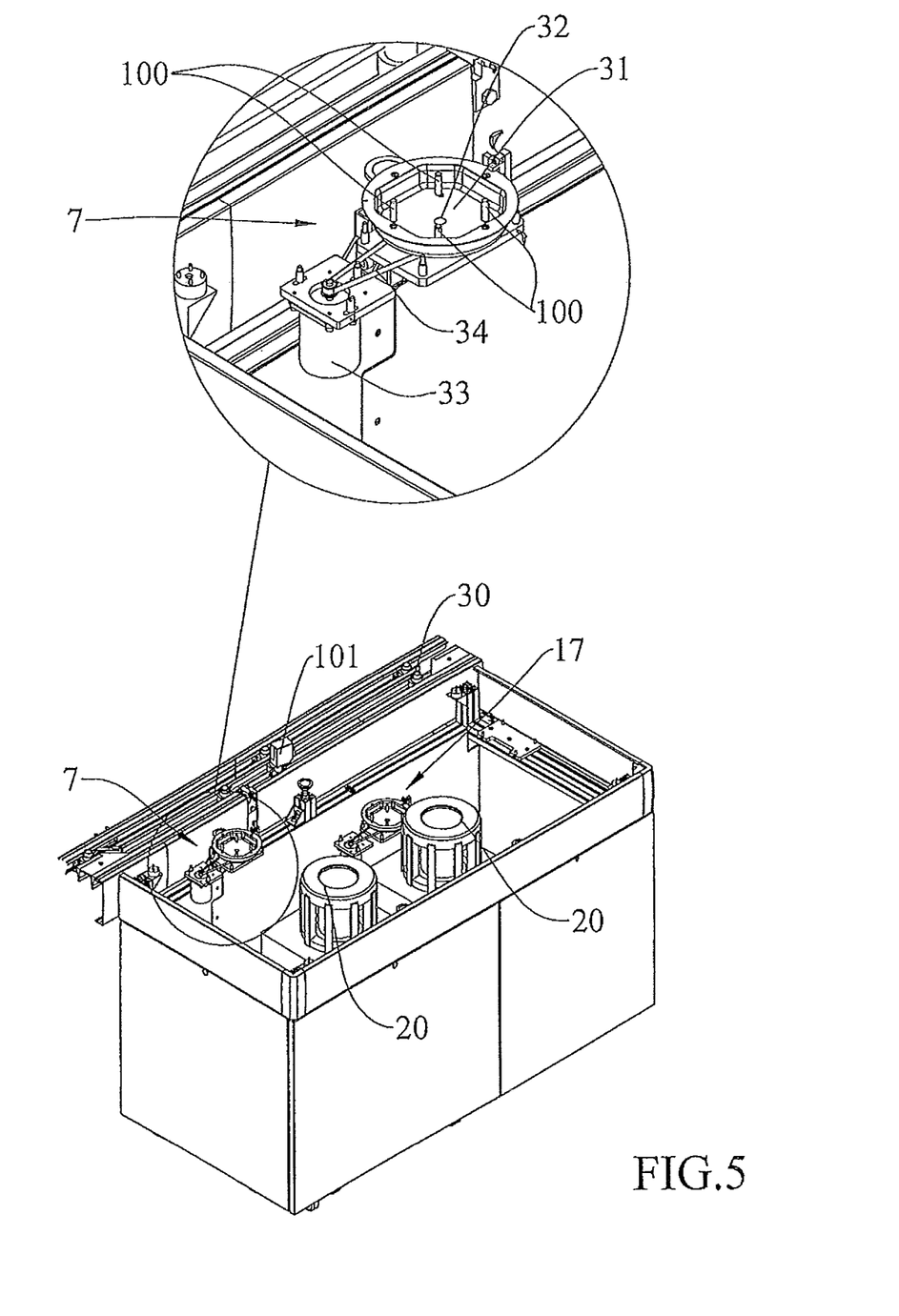
FIG. 5 shows a perspective view of the device with the bench removed.

The container orienting devices 7 and 17 serve the function of obtaining the correct orientation of the container 10 during the positioning process on the bench 3. Each of said container orienting devices 7 and 17, which are functionally equivalent to each other, consists of a plate 31, shaped as the octagonal base of the container 10, which rotates about its centre 32. Said plate 31 is provided with four orienting rods 100 (FIGS. 4 and 5). An electric motor 33 generates the rotation the plate 31 by means of belt 34 (FIG. 5). When the handling device 1 or 2 for test tubes and containers moves the container close to one of the two container orienting devices 7 and 17, the plate 31 turns until the four orienting rods 100 coincide with the four holes 15 on the resting surface of the container 10. At this time, the container 10 may be released, thus resting inside the plate 31, which rotates and returns to the initial position, thus ensuring the correct orientation to the container 10 for the handling devices 1 and 2 for test tubes and containers to be able to correctly reach the twenty positions according to the stored reference system.

Figure 3:
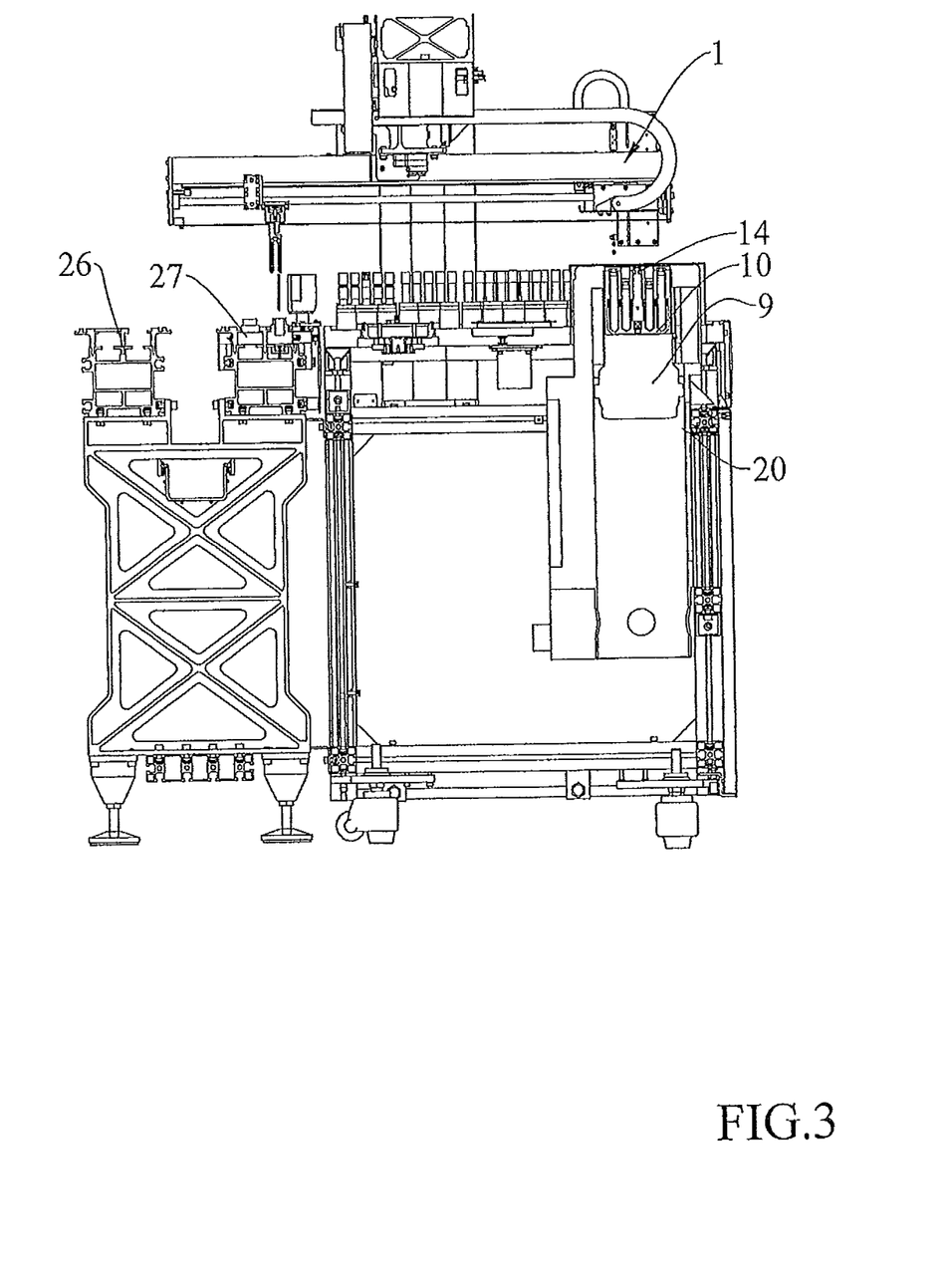
FIG. 3 shows a sectional view of the configuration in FIG. 2 taken along line III-III.

While transiting in the pipes 20 of a pneumatic mail system, the capsule 9 remains closed, and it automatically opens close to the receiving/dispatching stations 6 and 16, thus presenting the container 10 as shown in the FIG. 3. This allows the handling devices 1 and 2 for test tubes and containers to grip and move the container, thus ensuring a secure grip by means of the support 14.

Figure 2:
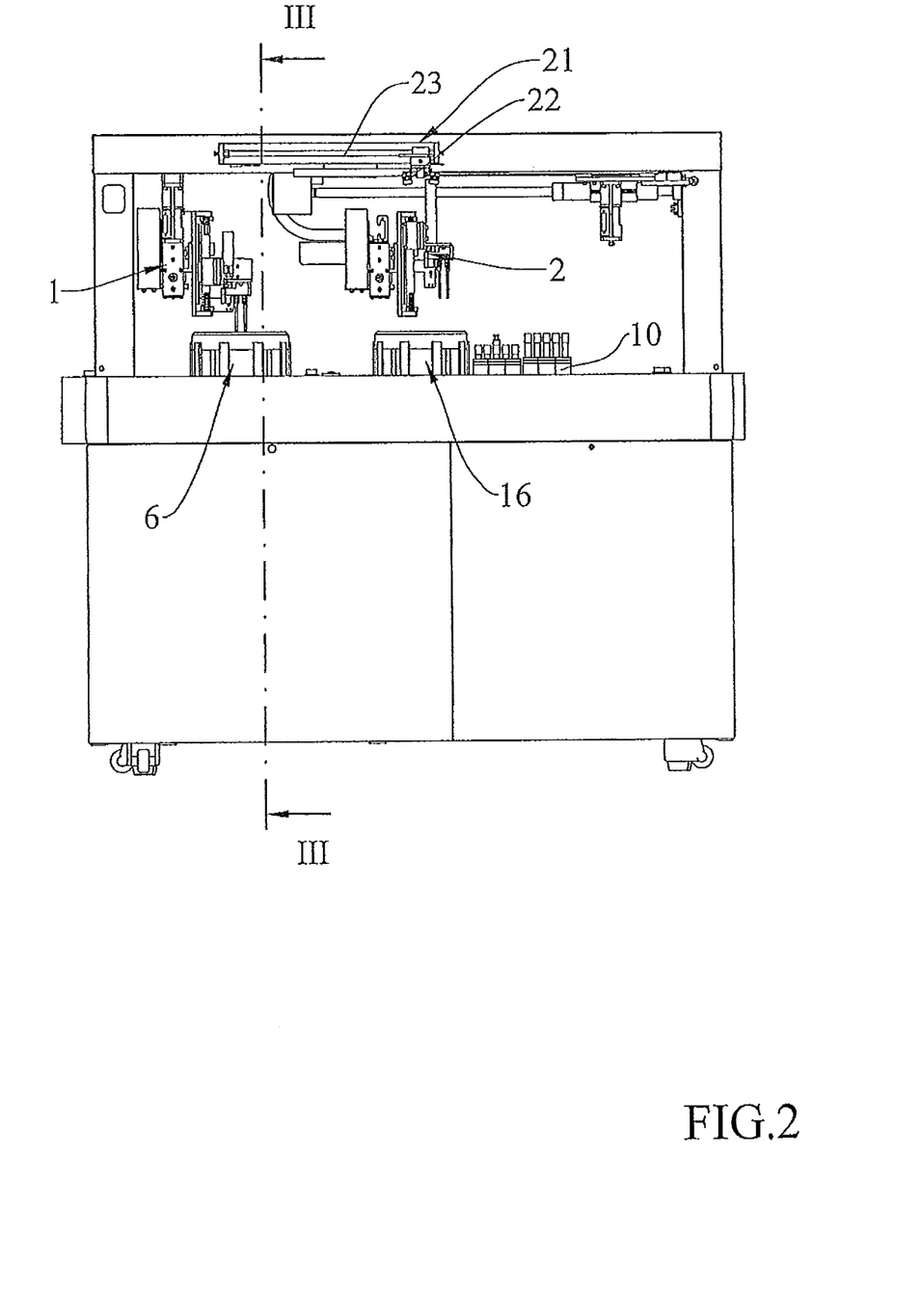
FIG. 2 shows a front view of the configuration in FIG. 1.

An identifying and checking device 21 (FIG. 1) for the arriving capsules and for the capsules to be dispatched is installed on the supporting structure of the handling devices 1 and 2 for test tubes and containers. In the described embodiment, said capsule identifying and checking device 21 consists of a camera 22, which may translate on a guide 23 and reach, according to the required operation, two positions exactly above the capsule receiving/dispatching stations 6 and 16 (FIG. 2).

Said capsule identifying and checking device 21 serves the function of checking the presence or absence of test tubes in the containers 10 arriving at the capsule receiving/dispatching stations 6 and 16. Upon the arrival of a capsule at one of the two stations, the camera 22 is placed over the correct position by sliding on the guide 23, so as to take a photograph of the arriving container 10.

The photograph of the container 10 arriving at the capsule receiving/dispatching station 6 from the hospital departments is processed by the control unit 24 for storing the locations of the container occupied by the test tubes. Such a piece of information is sent to the handling device 1 for test tubes and containers, which will unload the test tubes from the occupied positions only.

The photograph of the containers 10 arriving at the capsule receiving/dispatching station 16 from the specialized laboratories is used for verifying the actual absence of test tubes. If one or more test tubes are present in such containers, they are unloaded by the handling device 2 for test tubes and containers into the linear waiting test tube container 19 to then be unloaded into an interface module 25 (FIG. 1) adapted to automatically transport the test tubes.

Such an interface module 25 consists of a conveyor belt 26 on which test tubes containers or carriers 27 move (FIGS. 3 and 4). Said carriers 27, sliding on the conveyor belt, transport the test tubes along a conveyor belt to the various preparing and testing modules, according to the tests to which the test tubes must be subjected.

The portion of conveyor belt interfacing with the test tube loading and unloading system is provided with a test tube identification system 28 serving the function of identifying the test tube placed by the test tube handling device 1 from the bench 3 to the test tube carrier 27 in the unloading point 29 (FIG. 4).

In the described embodiment, the test tube is identified by reading the barcode on the label placed on the test tube by a suitable barcode reading device 101 (FIG. 5).

On the conveyor belt there is a test tube loading point 30 from where the arriving test tubes are picked by the test tube handling device 2 and placed in the containers 10 at the loading area 5 on the bench 3.

For a better understanding of the described apparatus, the steps of the process for unloading a container 10 arriving at the capsule receiving/dispatching station 6 are listed below:

a capsule 9 arrives at the capsule receiving/dispatching station;

the capsule identifying and checking device 21 places the camera 22 by sliding it along the guide 23, so that is may take a photograph of the container 10 contained in the capsule 9 arriving at the capsule receiving/dispatching station 6;

the information on the presence and position of the test tubes inside the container 10 is sent from the control unit 24 to the handling device 1 for test tubes and containers;

the handling device 1 for test tubes and containers grips the container 10 by means of the support 14 and moves the container 10 in the container orienting device 7;

once the container 10 has been placed according to the right orientation in the plate 31, it is ready to be emptied of the test tubes therein;

the handling device 1 for test tubes and containers, according to the information received from the control unit 24 concerning the presence or absence of the test tubes, only checks one by one the positions in which the information on test tube presence was obtained;

the test tube is gripped by the handling device 1 for test tubes and containers and placed in the carrier 27 at the unloading point 29 where the test tube identifying device 28 detects the identity thereof;

according to the identity and type of processing required, the test tube may be transported by the carrier 27 along the conveyor belt and then possibly diverted to the preparing and testing modules interfacing with such a conveyor belt, or presented at the subsequent test tube loading point 30 to be picked and placed in a container 10 in the loading area 5 and sent to the specialized test laboratories by means of the pneumatic mail system;

once all the test tubes of the container 10 placed on the plate 31 of the container orienting device 7 have been removed, the handling device 1 for test tubes and containers grips the container 10 and places it into the open capsule 9 at the capsule receiving/dispatching station 6 to be sent back to a hospital department where new test tubes to be tested may be loaded therein;

if a loaded capsule has reached the capsule receiving/dispatching station 6 in the meantime, the container 7 is moved from the plate 31 to the container transit position 8, waiting for the capsule which reached the capsule receiving/dispatching station 6 to be cleared of the new container.

The steps of the process for loading a container 10 arriving at the capsule receiving/dispatching station 16 are described below:

a capsule 9 arrives at the capsule receiving/dispatching station 16;

the capsule identifying and checking device 21 places the camera 22 by sliding it along the guide 23, so that is may take a photograph of the container 17 contained in the capsule 9 arriving at the capsule receiving/dispatching station 16;

the information on the presence and position of the test tubes in the container is sent from the control unit 24 to the handling device 2 for test tubes and containers;

the containers arriving at the capsule receiving/dispatching station 16 are generally empty and ready to be loaded with test tubes from the interface module 25, but in some cases, the specialized laboratories from where such containers come, send test tubes which require to be further processed by the modules which interface with the conveyor belt 26, as previously described;

in this case, the camera 22 records the container positions occupied by the test tubes and such a piece of information is sent to the handling device 2 for test tubes and containers;

the handling device 2 for test tubes and containers grips the container 10 by means of the support 14 and moves the container in the container orienting device 17;

once the container 10 has been placed according to the right orientation in the plate of the container orienting device 17, the container is moved into one of the twenty-two available test tube loading positions 18;

the handling device 2 for test tubes and containers, according to the information received from the control unit 24 concerning the presence or absence of the test tubes, only checks one by one the positions in which the information on test tube presence was obtained;

such test tubes are moved in the linear waiting test tube container 19 to then be unloaded at a later time at the test tube unloading point 29;

once the complete emptiness of the container has been defined, the handling device 2 for test tubes and containers may load the containers with test tubes arriving at the test loading point 30;

once the container has been loaded with the test tubes, it is ready to be dispatched: the handling device 2 for test tubes and containers grips the container and inserts it into the capsule 9 waiting at the capsule receiving/dispatching station 16.

The described apparatus according to the present invention allows to implement a completely automatic process, also including the steps of loading and unloading the containers transported by means of a pneumatic mail system, thus minimizing human intervention to the greatest possible extent during the various steps of the process, decreasing the risks of error, and preserving the operator safety.

The invention claimed is:

1. An apparatus for automatically loading and unloading biological material test tubes, said test tubes being transported into and from a capsule, said capsule being suitable for a pneumatic mail system comprising a pipe network, said test tubes being supported by a test tube container which is removably accommodated in said capsule, which comprises:
a conveyor comprising a loading and unloading interface adapted to automatically transport single biological material test tubes to biological material preparing and testing modules;
a receiving/dispatching station for the capsules connected by pipes of said pneumatic mail system to/from biological material collecting departments;
a receiving/dispatching station for capsules connected by additional pipes of said pneumatic mail system to/from biological material testing departments;
handling devices adapted to handle arriving test tube containers and single test tubes, said test tubes and test tube containers being dispatched to a bench, said bench including a loading area and an unloading area for single test tubes and test tube containers;
material identifying and checking devices;
rotational orienting devices placed on said bench for test tube containers picked up by said devices from the capsules at said receiving/dispatching station with a random orientation, said rotational orienting devices being able to rotate said containers from a random orientation to a correct orientation of the container; and
a control unit adapted to coordinate said handling devices during the loading and unloading operations,
wherein said rotational orienting devices of the test tube containers comprise a plate which rotates about its center, said plate including orienting rods and an electric motor which is adapted to control the rotation of the plate, said plate first turning so that the orienting rods coincide with corresponding holes on the resting surface of the container, thus allowing the container to be released, with further turning to take the container to an oriented position which is suitable for loading/unloading test tubes from/to the interface of the conveyor, and
wherein the handling devices are able to correctly reach positions according to a reference system.

2. The apparatus according to claim 1, which further comprises waiting stations for the test tube containers.

3. An apparatus for automatically loading and unloading biological material test tubes, said test tubes being transported into and from a capsule, said capsule being suitable for a pneumatic mail system comprising a pipe network, said test tubes being supported by a test tube container which is removably accommodated in said capsule, which comprises:
a conveyor comprising a loading and unloading interface adapted to automatically transport single biological material test tubes to biological material preparing and testing modules;
a receiving/dispatching station for the capsules connected by pipes of said pneumatic mail system to/from biological material collecting departments;
a receiving/dispatching station for capsules connected by additional pipes of said pneumatic mail system to/from biological material testing departments;
handling devices adapted to handle arriving test tube containers and single test tubes, said test tubes and test tube containers being dispatched to a bench, said bench including a loading area and an unloading area for single test tubes and test tube containers;
material identifying and checking devices comprising a camera which translates along a guide, said camera being adapted to reach positions exactly over the capsule receiving/dispatching stations according to the required operation;
rotational orienting devices placed on said bench for test tube containers picked up by said devices from the capsules at said receiving/dispatching station with a random orientation, said rotational orienting devices being able to rotate said containers from a random orientation to a correct orientation of the container; and
a control unit adapted to coordinate said handling devices during the loading and unloading operations,
wherein the handling devices are able to correctly reach positions according to a reference system.

4. A method for automatically loading and unloading biological material test tubes into and from a capsule, said capsule being suitable for a pneumatic mail system, said test tubes being supported by a test tube container and are removably accommodated in said capsule, said method comprising:
a first method for unloading test tubes and loading/unloading test tube containers into and from a capsule, said capsules departing from/arriving by pipes of said pneumatic mail system at a collecting department of biological material disposed in test tubes, and
a second method for loading/unloading test tubes and test tube containers into and from a capsule, said capsules departing from/arriving by additional pipes of said pneumatic mail system at a biological material testing department,
said first method comprising the steps of identifying and checking the capsules arriving at a capsule receiving/ dispatching station by pipes of said pneumatic mail system from a biological material collecting department, wherein information on the presence and position of the test tubes inside the container is sent from a control unit to a handling device for test tubes and containers;

picking the container by the test tube and container handling device and handling the container to a container orienting device;

unloading the container into the orienting device for emptying the test tubes which are present according to a reference system;

checking the test tube and container handling device according to the information received from the control unit concerning the presence or absence of the test tubes, including checking the positions in which the information on test tube presence was obtained;

picking the test tubes by the test tube and container handling device, and positioning them at the unloading point, wherein a test tube identifying device detects the identity of the test tube, and according to its identity, the test tube is transported by a test tube carrier along a conveyor belt and towards preparing and testing modules interfacing with the conveyor belt or towards the loading point, whereby once all the test tubes have been removed from the container and placed in the container orientating device, the container is picked by the test tube and container handling device for placing it in the open capsule at the capsule receiving/dispatching station to be sent back to the pipes of said pneumatic mail system wherein said container may be loaded with new test tubes to be tested;

said second method comprising the steps of identifying and checking the capsules arriving at a capsule receiving/dispatching station by pipes of said pneumatic mail system from a biological material testing department, wherein information on the presence and position of the test tubes inside the container is sent from the control unit to the handling device for test tubes and containers;

picking the container by the test tube and container handling device and handling the container to a container orienting device;

unloading the container into the orienting device for emptying the test tubes which are present according to a reference system;

handling the container by means of the handling device for test tubes and containers from the container orienting device to an appropriate loading area;

checking the test tube and container handling device according to the information received from the control unit concerning the presence or absence of the test tubes, including checking the positions in which the information on test tube presence was obtained; and picking the test tubes by the test tube and container handling device, and positioning the test tubes waiting for being unloaded at an appropriate unloading point on the conveyor belt, wherein once the complete emptiness of the container has been defined, the test tubes arriving at the test tube loading point are loaded on the conveyor belt by the test tube and container handling device, and picking the container loaded with test tubes by the test tube and container handling device, and inserting the container into the capsule waiting for dispatch to a testing department at the capsule receiving/dispatching station by pipes of said pneumatic mail system.

5. The method according to claim 4, wherein said step of identifying and checking comprises photographing the test tube container contained in the capsule arriving at the capsule receiving/dispatching stations.

6. The method according to claim 4, which comprises a step of orienting the test tube container which includes the rotation of a plate about its center, said plate including orienting rods, so that said orienting rods coincide with corresponding holes on the resting surface of the container, which allows the container to be released, said plate further turning for taking the container to an oriented position which is suitable for loading/unloading test tubes to/from the interface of the conveyor.

* * * * *